(12) United States Patent
Henderson

(10) Patent No.: US 12,060,431 B2
(45) Date of Patent: *Aug. 13, 2024

(54) DOSING REGIMEN OF COMBINATION OF ANTICD20 AND ANTI-BlyS ANTIBODIES

(71) Applicant: GLAXOSMITHKLINE INTELLECTUAL PROPERTY MANAGEMENT LIMITED, Stevenage (GB)

(72) Inventor: Robert B. Henderson, Stevenage (GB)

(73) Assignees: GlaxoSmithKline Intellectual Property Management Limited, Stevenage (GB); GlaxoSmithKline Intellectual Property Limited, Stevenage (GB)

( * ) Notice: Subject to any disclaimer, the term of this patent is extended or adjusted under 35 U.S.C. 154(b) by 253 days.

This patent is subject to a terminal disclaimer.

(21) Appl. No.: 17/519,063

(22) Filed: Nov. 4, 2021

(65) Prior Publication Data

US 2022/0195062 A1 Jun. 23, 2022

Related U.S. Application Data

(63) Continuation of application No. 15/762,195, filed as application No. PCT/EP2016/072443 on Sep. 21, 2016, now Pat. No. 11,180,569.

(30) Foreign Application Priority Data

Sep. 25, 2015 (GB) ..................... 1516836

(51) Int. Cl.
*C07K 16/28* (2006.01)
*A61P 37/02* (2006.01)
*A61K 39/00* (2006.01)

(52) U.S. Cl.
CPC .......... *C07K 16/2887* (2013.01); *A61P 37/02* (2018.01); *C07K 16/2875* (2013.01); *A61K 2039/507* (2013.01); *C07K 2317/76* (2013.01)

(58) Field of Classification Search
None
See application file for complete search history.

(56) References Cited

U.S. PATENT DOCUMENTS 11,180,569 B2 * 11/2021 Henderson ......... C07K 16/2887
2008/0299117 A1 * 12/2008 Barron ..................... A61P 37/02
424/133.1

FOREIGN PATENT DOCUMENTS

WO WO 2005/000351 A2 1/2005
WO WO 2005/005462 A2 1/2005

OTHER PUBLICATIONS

Lloyd et al. (Protein Engineering, Design & Selection 2009, 22:159-168).*
Barile-Fabris et al. (Curr Rheumatol Rep 2014 16:440).*
Changhai Ding, et al. Biodrugs, 22(4): 239-249 (Jan. 1, 2008).
W. Stohl, et al. Clinical Immunology, 121(1): 1-12 (Oct. 1, 2006).
Qian Gong, et al. The Journal of Immunology, 174(2): 817-826 (Jan. 15, 2005).
W. Lin, et al. Arthritis & Rheumatology, 67(1): 215-224 (Jan. 1, 2015).
Lazaro Estibaliz, et al. Joint Bone Spine, pp. 1-8 (Sep. 21, 2016).
S. De Vita, et al. Clinical and Experimental Rheumatology, 32(4): 490-494 (Jul. 23, 2014).

* cited by examiner

*Primary Examiner* — Sharon X Wen
(74) *Attorney, Agent, or Firm* — Kelly A. Gauger

(57) ABSTRACT

The present invention relates to a CD20 binding antibody which is capable of depleting B cells, and a BLyS binding antibody which is capable of antagonizing BLyS, as a combination for use in the treatment of an autoimmune disorder. The invention also relates to dosages, duration of treatment and time lapses between administration of the CD20 binding antibody which is capable of depleting B cells, and the BLyS binding antibody which is capable of antagonizing BLyS.

10 Claims, No Drawings

DOSING REGIMEN OF COMBINATION OF ANTICD20 AND ANTI-BlyS ANTIBODIES

BACKGROUND

Autoimmune diseases, such as Sjögren's syndrome, rheumatoid arthritis, multiple sclerosis, autoimmune hepatitis and inflammatory bowel disease have complex pathogeneses and the factors which cause these disorders are not well understood. However, all of them arise from a dysfunction of the immune system, interpreting self components as foreign antigens. The field of immunotherapy has undergone a major rejuvenation with the development of monoclonal antibodies and fusion proteins targeting specialized receptors of T and B lymphocytes or cytokines relevant for the differentiation of these cells (Chatenoud 2015; Curr Opin Pharmacol 23: 92-97).

Examples of autoimmune disorders that may be treated by targeting B lymphocytes include lupus, rheumatoid arthritis, juvenile rheumatoid arthritis, vasculitis, Sjögren's syndrome, Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, organ or transplant rejection in a patient, GRAFT vs host disease, Reynaud's syndrome and glomerulonephritis.

Sjögren's syndrome (pSS) is a common autoimmune disease manifested by sicca symptoms, constitutional findings and potentially severe, life-threatening organ-specific extra-glandular manifestations. It is characterised by a combination of features including oral and ocular dryness, which can be disabling; ocular signs including objective evidence for involvement; salivary gland involvement including abnormal appearance of salivary glands; and presence of antibodies to Ro and/or La. Patients may also experience severe, variable and unpredictable fatigue, which is similar in character and severity to that of patients with SLE (systemic lupus erythematosus). Similarly, fibromyalgia and widespread chronic pain are found in 5% of pSS patients, again, comparable to SLE. Extra-glandular manifestations occur in 20 to 40% of patients and include rashes, peripheral neuropathy, Hashimoto's thyroiditis, non-erosive arthritis, arthralgia, vasculitis, interstitial lung disease, B-cell lymphoma, pancreatitis, primary biliary cirrhosis, autoimmune hepatitis and renal disease.

B cells are thought to play a central pathogenic role in pSS. There are no disease modifying treatments for this disease and existing approved therapies consist of symptomatic treatments that do not address the autoimmune pathology. Therefore, substantial unmet medical need exists for a disease modifying therapy; one that can stop B-cell mediated autoimmune damage, alleviate glandular as well as constitutional symptoms and ameliorate extra-glandular target organ manifestations.

B Lymphocyte Stimulator (BlyS, also known as BAFF) promotes B-cell maturation, proliferation and survival. Transgenic mice that over-express this cytokine develop features of SLE, and go on to develop clinical characteristics of primary Sjögren's syndrome (Mackay, 1999; J Exp Med: 1697-710). In recent years, several studies have focused on elucidating the role of BLyS in primary Sjögren's syndrome. Serum BLyS levels were demonstrated to be increased, and to correlate with, levels of anti-Ro/SS-A antibodies and rheumatoid factor (RF) in patients with primary Sjögren's syndrome (Marlette, 2003; Ann Rheum Dis 62:168-71) and elevated levels of BLyS have been detected in saliva (Daridon, 2007; Arthritis Rheumatol 56:1134-44; Lavie, 2008; Scand J Immunol 67:185-92).

The CD20 molecule (also called human B-lymphocyte-restricted differentiation antigen or Bp35) is a hydrophobic transmembrane protein with a molecular weight of approximately 35 kD located on pre-B and mature B lymphocytes. CD20 is found on the surface of greater than 90% of B cells from peripheral blood or lymphoid organs and is expressed during early pre-B cell development and remains until plasma cell differentiation. CD20 is present on both normal B cells as well as malignant B cells.

CD20 is involved in regulating an early step(s) in the activation and differentiation process of B cells and it is an important target for antibody mediated therapy to control or kill B cells involved in autoimmune disorders.

Though there have been many recent advances in the treatment of Sjögren's syndrome, there remains a need for more effective and/or enhanced treatment of an individual suffering the effects of the syndrome. The current invention addresses this need.

SUMMARY OF INVENTION

The present invention describes a CD20 binding antibody which is capable of depleting B cells, and a BLyS binding antibody which is capable of antagonizing BLyS, as a combination for use in the treatment of an autoimmune disorder, wherein the BLyS binding antibody is administered to a human in need thereof for a period of at least 12 weeks, and the CD20 binding antibody is administered to the human in need thereof at least two weeks after the first dose of the BLyS binding antibody, and the administration of the BLyS binding antibody continues for at least 4 weeks after the last dose of the CD 20 binding antibody.

The invention also provides dosages, duration of treatment and time lapses between administration of the CD20 binding antibody which is capable of depleting B cells, and the BLyS binding antibody which is capable of antagonizing BLyS. Also provided are examples of autoimmune disorders to be treated with the invention.

DETAILED DESCRIPTION

Administration of anti-CD20 therapy has been shown to result in an increase in serum BLyS (Cambridge, 2006; Arthritis Rheumatol 54:723-32; Lavie, 2006; Ann Rheum Dis 66:700-203; Pers, 2007; Arthritis Rheumatol 56:1464-77). This increase is linked both to the disappearance of BLyS-binding B cells in peripheral blood, as well as to a true homeostatic feedback characterized by increased BLyS mRNA expression in monocytes after rituximab treatment (Toubi, 2007; Ann Rheum Dis 66:818-20; Lavie, 2007; Ann Rheum Dis 66:700-703). The inventors of the present invention consider that this increase in BLyS after rituximab treatment could favour the stimulation of new autoimmune B cells and possibly explains the waning clinical improvement over time seen in clinical studies of rituximab in patients with Sjögren's syndrome.

Anti-BLyS and anti-CD20 therapeutics operate through different but complementary mechanisms: anti-BLyS (e.g. belimumab) therapeutics rapidly increase peripheral memory B cells (possibly by mobilization/redistribution of tissue B cells), decrease naive, activated and plasma B cell subsets, and increase stringency on B cell selection during reconstitution; while anti-CD20 (e.g. rituximab) therapeutics eliminate peripheral B cells through complement dependent cytotoxicity (CDC) and antibody-dependent cell-mediated cytotoxicity (ADCC). The inventors of the present invention believe that paired together, these two mechanisms may achieve synergistic effects through improved depletion of memory and germinal centre tissue B cells and increased stringency during B cell reconstitution with additive effects through more efficient targeting of circulating plasma cells.

Pre-clinical evidence supporting the hypothesis that dual B-cell targeted immunotherapy maybe more efficacious than mono-therapy, has been generated in a human-CD20 expressing mouse model. This model demonstrated limited tissue depletion with anti-CD20 antibody mono-therapy but increased efficacy of anti-CD20 therapy when B cells were mobilized into the peripheral blood through concomitant inhibition of adhesion (Gong, 2005; J Immunol 174:817-826). The combined effect of administration of mouse BLyS receptor (BR3)-Fc and anti-hCD20 in this model leads to more effective tissue B cell depletion. Similar observations have been made in SLE models (Lin, 2015; Arthritis Rheumatol. 67: 215-224) where dual targeting resulted in greater efficacy with increased tissue B cell depletion, greater reduction in a range of auto-antibody levels and significant decreases in total IgG1, IgG2b, IgG3, IgM and IgA when compared to BLyS inhibition and CD20 B-cell depletion alone. Total plasma cells in the long lived bone marrow niche, thought to be less sensitive to immunotherapy, were not affected relative to monotherapy with the exception of IgG1+ plasma cells. Assessment of the translatability of the IgG reductions to humans are difficult to make due to species differences in B-cell biology and different treatments; however the mouse data raises the hypothetical risk that immunoglobulin levels may reduce more with combination treatment.

The present invention describes a CD20 binding antibody which is capable of depleting B cells, and a BLyS binding antibody which is capable of antagonizing BLyS, as a combination for use in the treatment of an autoimmune disorder, wherein the BLyS binding antibody is administered to a human in need thereof for a period of at least 24 weeks, the CD20 binding antibody is administered to the human in need thereof at least simultaneously to the first dose of the BLyS binding antibody and the administration of the BLyS binding antibody continues for at least 4 weeks after the last dose of the CD20 binding antibody.

The term "antibody" herein is used in the broadest sense and specifically covers monoclonal antibodies, polyclonal antibodies, multispecific antibodies and antibody fragments exhibiting the desired biological activity.

B-cell therapies are designed to eliminate either the majority of B cells (general depletion) or only some B-cell populations (selective depletion). In both cases, depletion is achieved through 2 principal mechanisms: direct killing by monoclonal antibodies against B-cell surface molecules CD19, CD20 (e.g. rituximab, ofatumumab, ocrelizumab) and CD22 (e.g. epratuzumab), and attrition due to inhibition of B-cell survival factors BLyS (e.g. belimumab) and APRIL (e.g. atacicept). Other possible ways to target B cells include inhibiting their activation through binding of inhibitory receptors or neutralizing cytokines that play a key role in B cell activation, maturation and/or differentiation (Ramos-Casals 2012; Am. J. Med. 125: 327-336).

B cell depletion is a direct approach to get rid of malignant B cells or of the source of pathogenic antibodies. It can also be seen as a strategy to act on B cells as antigen-presenting cells or as cells capable of modulating immune responses (regulatory B cells). There are a number of B cell depleting agents used in a variety of autoimmune disorders, including rheumatoid arthritis, immune thrombocytopenic purpura, autoimmune hemolytic anemia, systemic lupus erythematosus, vasculitis, dermatomyositis, multiple sclerosis and type 1 diabetes (Chatenoud 2015; Curr Opin Pharmacol 23: 92-97). CD20 binding antibodies of the invention target the CD20 antigen on B cells and are successfully used in the clinic for the depletion of B cells to treat various forms of cancer and autoimmune diseases (Boross 2012; Am J Cancer Res 2: 676-690).

BLyS binding antibodies of the invention which are capable of antagonizing BLyS may decrease or inhibit BLyS-induced signal transduction. For example, BLyS binding antibodies of the invention which are capable of antagonizing BLyS may disrupt the interaction between BLyS and its receptor to inhibit or downregulate BLyS-induced signal transduction. BLyS binding antibodies of the invention which are capable of antagonizing BLyS and which do not prevent BLyS from binding its receptor but inhibit or downregulate BLyS-induced signal transduction also can be used in accordance with the invention set forth herein. In particular, BLyS binding antibodies of the invention which are capable of antagonizing BLyS and which prevent BlyS induced signal transduction by specifically recognizing the unbound BLyS protein, receptor-bound BlyS protein, or both unbound and receptor-bound BLyS protein can be used in accordance with the invention set forth herein. The ability of a BLyS binding antibody of the invention which is capable of antagonizing BLyS to inhibit or downregulate BLyS induced signal transduction may be determined by techniques known in the art. For example, BLyS-induced receptor activation and the activation of signaling molecules can be determined by detecting the phosphorylation (e.g., tyrosine or serine/threonine) of the receptor or a signaling molecule by immunoprecipitation followed by western blot analysis.

In one embodiment of the present invention, the CD20 binding antibody which is capable of depleting B cells is administered to the human in need thereof at least two weeks after the first dose of the BLyS binding antibody which is capable of antagonizing BLyS.

In another embodiment, the CD20 binding antibody which is capable of depleting B cells is administered to the human in need thereof at least twice between weeks 2 and 20 after the first dose of the BLyS binding antibody which is capable of antagonizing BLyS. For example, the CD20 binding antibody which is capable of depleting B cells is administered to the human in need thereof at least at weeks 2 and 20, weeks 4 and 18, weeks 6 and 16, weeks 8 and 14 or weeks 10 and 12 after the first dose of the BLyS binding antibody which is capable of antagonizing BLyS.

For example, the CD20 binding antibody which is capable of depleting B cells is administered to the human in need thereof at weeks 4 and 6, weeks 6 and 10, weeks 8 and 10 or weeks 8 and 12 after the first dose of the BLyS binding antibody.

In one embodiment, the CD20 binding antibody which is capable of depleting B cells is administered to the human in need thereof 8 and 10 weeks after the first dose of the BLyS binding antibody.

In one embodiment, the CD20 binding antibody which is capable of depleting B cells is administered to the human in need thereof 4 and 6 weeks after the first dose of the BLyS binding antibody.

Additional doses of the CD20 binding antibody which is capable of depleting B cells may be administered at least 24 weeks after the start of the treatment with the BLyS binding antibody. For example, third and fourth doses of the CD20 binding antibody which is capable of depleting B cells may be administered at weeks 24 and 48, or weeks 24 and 25, 26, 27, 28, 29, 30, 31, 32, 33, 34, 35, 36, 37, 38, 39, 40, 41, 42, 43, 44, 45, 46, 47 or 48. Similarly, a fourth dose may be administered at least 48 weeks after the start of the treatment with the BLyS binding antibody. For example, a fourth dose may be administered at week 48, 49, 50, 51, 52, 53, 54, 55, 56, 57, 58, 59, 60, 61, 62, 63, 64, 65, 66, 67, 68, 69, 70, 71 or 72.

In one embodiment, the BLyS binding antibody which is capable of antagonizing BLyS is administered to the human in need thereof once per week.

In yet another embodiment, the BLyS binding antibody which is capable of antagonizing BLyS is administered to the human in need thereof for a period of 24 weeks.

In yet another embodiment, the BLyS binding antibody which is capable of antagonizing BLyS is administered to the human in need thereof for a period of 52 weeks.

In one embodiment, the CD20 binding antibody which is capable of depleting B cells, and the BLyS binding antibody which is capable of antagonizing BLyS, as a combination for use in the treatment of an autoimmune disorder increase the immunological tolerance of the human in need thereof and/or induce a long term remission of said autoimmune disorder. Such increase in immunological tolerance and/or induction of long term remission can be measured by clinical or biomarker assessment or by use of a suitable disease severity score, for example ESSDAI for Sjögren's syndrome or SELENA SLEDAI for SLE.

In one embodiment, the BLyS binding antibody is systematically administered to the human in need thereof for a maximum period of 6 months after the last dose of the CD20 binding antibody, for example, it is administered for no longer than 3 months or no longer than 4 months after the last dose of the CD20 binding antibody The dosing of the CD20 antibody after the bLyS antibody allows the opportunity for the B cells to mobilize from lymphoid tissues. The mobilization of B cells is known to occur 1 week after bLyS antibody dosing however, in order to allow suitable time for the anti bLyS antibody to take effect whilst not simultaneously administering an anti CD20 antibody to patients being given background immunosuppressant's a carefully balanced dosage regimen is required.

For example in one embodiment the immunosuppressant's will be discontinued at Week 4 prior to the first dose of rituximab after 4 weeks of belimumab treatment.

In one embodiment, the BLyS binding antibody which is capable of antagonizing BLyS is belimumab.

Belimumab is a human monoclonal antibody that inhibits B-lymphocyte stimulator (BLyS). The complete amino acid and corresponding nucleic acid sequence for this antibody may be found in U.S. Pat. No. 7,138,501.

Belimumab can be administered by various routes of administration, typically parenteral. This is intended to include intravenous, intramuscular, subcutaneous, rectal and vaginal. Effective dosages will depend on the condition of the patient, age, weight, or any other treatments, among other factors. The administration may be effected by various protocols, e.g., weekly, bi-weekly, or monthly, dependent on the dosage administered and patient response.

In one embodiment, belimumab is administered as a subcutaneous injection. In one such embodiment, belimumab is administered at a dosage of 200 mg. In a further such embodiment, belimumab is administered once per week at a dosage of 200 mg.

In a further embodiment, belimumab is administered by intravenous injection. Depending on the type and severity of the disease, about 1 μg/kg to 50 mg/kg of bodyweight or more specifically between about 0.1 mg/kg to 20 mg/kg of bodyweight) of belimumab is a candidate initial dosage for administration to the patient, whether, for example, by one or more separate administrations, or by continuous infusion. More specifically the dosage of the antibody will be in the range from about 0.05 mg antibody/kg of bodyweight to about 10 mg antibody/kg of bodyweight. In one embodiment when Belimumab is given intravenously the recommended dosage regimen is 10 mg/kg. In a further embodiment belimumab is given at 10 mg/kg at 2-week intervals for the first 3 doses and at 4-week intervals thereafter.

In another embodiment, the CD20 binding antibody which is capable of depleting B cells is rituximab.

Rituximab is a chimeric gamma 1 anti-human CD20 antibody. The complete amino acid and corresponding nucleic acid sequence for this antibody may be found in U.S. Pat. No. 5,736,137.

Rituximab may be administered by various routes of administration, typically parenteral. This is intended to include intravenous, intramuscular, subcutaneous, rectal and vaginal. Effective dosages will depend on the condition of the patient, age, weight, or any other treatments, among other factors. The administration may be effected by various protocols, e.g., weekly, bi-weekly, or monthly, dependent on the dosage administered and patient response.

In one embodiment, rituximab is administered as an intravenous infusion.

In another embodiment, rituximab is administered at a dosage of 1000 mg.

Other dosages at which rituximab may be administered include a dosage of 500 mg; a dosage of 375 mg/m$^2$ IV once weekly for 4 doses at 6 month intervals to a maximum of 16 doses; a dosage of 375 mg/m$^2$ IV every 8 weeks for 12 doses; a dosage of 375 mg/m$^2$ IV once weekly for 4 doses, and a dosage of 375 mg/m$^2$ IV once weekly for 4 doses.

In one embodiment, rituximab is administered as a subcutaneous injection.

In another embodiment, rituximab is administered at a dosage of 1400 mg.

In one such embodiment the rituximab is at a concentration of 120 mg/ml. In yet a further embodiment patients who receive a subcutaneous administration must first have received an intravenous dose.

In one embodiment, the CD20 binding antibody which is capable of depleting B cells is ofatumumab.

Ofatumumab is a human monoclonal anti-human CD20 antibody. The complete amino acid and corresponding nucleic acid sequence for this antibody may be found in U.S. Pat. No. 8,529,902.

Ofatumumab may be administered by various routes of administration, typically parenteral. This is intended to include intravenous, intramuscular, subcutaneous, rectal and vaginal. Effective dosages will depend on the condition of the patient, age, weight, or any other treatments, among other factors.

As an example, ofatumumab may be administered as an intravenous infusion, at a dosage of 1000 mg.

Ofatumumab may also be administered at an initial dosage of 300 mg, followed by 1,000 mg on Day 8 (Cycle 1). Ofatumumab may also be administered at an initial dosage of 2000 mg weekly for 7 doses, followed 4 weeks later by 2,000 mg every 4 weeks for 4 doses.

As established earlier, any other CD20 binding antibodies capable of depleting B cells will be equally suitable at similar dosing regimens schedules in the context of the invention.

Other types of administration of both antibodies which may become available are contemplated within the context of the invention.

In one embodiment of the present invention, the autoimmune disorder is a B-cell regulated autoimmune disorder.

An autoimmune disorder is a disorder arising from and directed against an individual's own tissues or organs or a co-segregate or manifestation thereof or resulting condition therefrom.

The autoimmune disorder to be treated with the invention may be selected from the group consisting of lupus, for example systemic lupus erythramatosus, lupus nephritis, cutaneous or discoid lupus; rheumatoid arthritis, juvenile rheumatoid arthritis, vasculitis, Jorgen's syndrome, Wegener's disease, inflammatory bowel disease, idiopathic thrombocytopenic purpura (ITP), thrombotic thrombocytopenic purpura (TTP), autoimmune thrombocytopenia, multiple sclerosis, psoriasis, IgA nephropathy, IgM polyneuropathies, myasthenia gravis, vasculitis, diabetes mellitus, organ or transplant rejection in a patient, GRAFT vs host disease, Reynaud's syndrome and glomerulonephritis.

In one embodiment, the autoimmune disorder is selected from the group consisting of lupus, rheumatoid arthritis, juvenile rheumatoid arthritis, vasculitis and Sjögren's syndrome.

In yet another embodiment, the autoimmune disorder is Sjögren's syndrome.

In yet another embodiment, the autoimmune disorder is Systemic lupus erythematosus (SLE).

EXAMPLES

Example 1

In this prophetic example, the synergistic activity of the BLyS and CD20 binding antibodies will be tested.

Overall Design and Plan of the Study

This is a randomized, double blind (sponsor open), comparative, multi-centre study to evaluate the safety and efficacy of subcutaneous belimumab and intravenous rituximab co-administration in subjects with primary Sjögren's syndrome.

This study is designed to understand the safety and tolerability profile of belimumab/rituximab co-administration and of belimumab monotherapy; and to evaluate whether either co-administration therapy or belimumab monotherapy has a substantive effect on disease activity. It is also designed to understand the underlying immunological mechanisms impacted by belimumab monotherapy compared to placebo or rituximab monotherapy and to determine if there is a mechanistic difference between monotherapy and co-administration therapy. Disease activity assessment at week 52 will allow determination of whether any clinical effects of co-administration therapy achieved at week 24 are sustained after discontinuation of therapy and/or whether chronic treatment with belimumab monotherapy is effective.

Once a sufficient number of subjects have completed week 24, interim analyses and sample size re-estimation will be conducted. The results of the interim analyses will be reviewed by the iSRC, details of which will be outlined in the iSRC charter. Dependent on these results, the study will continue as planned, continue with modifications or may be stopped.

Treatment Arms and Duration

Patients will be randomized 1:2:2:2 to one of the four treatment arms below.

Placebo Arm: Patients will receive belimumab placebo injections and rituximab placebo infusions.

Belimumab Monotherapy Arm: Patients will receive 200 mg weekly subcutaneous injections of belimumab for 52 weeks and placebo rituximab infusions at weeks 4 and 6 or at weeks 8 and 10.

Co-administration Therapy Arm: Patients will receive belimumab 200 mg weekly subcutaneous injections for 24 weeks followed by weekly placebo belimumab injections to week 52 with rituximab 1,000 mg intravenously at weeks 4 and 6 or weeks 8 and 10.

Rituximab Monotherapy Arm: Patients will receive 1,000 mg IV infusions of rituximab at Weeks 8 and 10 and weekly subcutaneous injections of placebo belimumab for 52 weeks.

The total number of subjects recruited will be determined through an ongoing review of the data and sample size re-estimation. Following interim analyses, a number of actions could be taken: the study may continue as planned; one or more treatment arms may be dropped; the number of subjects in some or all treatment arms may be increased following sample size re-estimation, up to a maximum of 120 total subjects in the study where up to a maximum of 25, 45, 30 and 20 will be randomized to placebo, belimumab monotherapy, co-administration therapy and rituximab monotherapy respectively. The randomisation ratio will vary dependent on the number of treatment arms continuing following the interim analysis.

Subjects in all arms will be followed until week 52 (defined as study completion). At week 52, subjects with CD19+ B-cell levels below the lower limit of normal (or less than 90% of baseline, if baseline value was below LLN) will enter an individualized safety follow up phase and return to the clinic for visits every 12 weeks with monthly calls between visits to evaluate subjects for any AEs and to check concomitant medications.

Results

Primary Analyses. All safety evaluations will be based on the safety population. Clinical interpretation will be based upon review and displays of adverse events, disease related events, laboratory values and vital signs. The principle consideration in this evaluation will be the investigator-reported relationships of either adverse events or laboratory abnormalities to investigational product.

Secondary Analyses

Each endpoint will be considered individually and at the treatment level where comparisons between treatment groups would be made on any changes observed.

The relationship between the mechanistic (e.g. salivary gland B cell quantification) and clinical effects (e.g., stimulated salivary flow) will be graphically presented and analysed using an appropriate statistical model identifying any trends. The model will determine whether the mechanistic effect significantly explains or predicts the effect on the clinical endpoints (e.g., ESSDAI score). This may be conducted through comparing statistical models; incorporating different explanatory terms (ie. mechanistic endpoints) with the 'null' model (no mechanistic endpoints); or, if deemed appropriate, multivariate statistical methods may also be applied to determine the relationship between the key endpoints. The consistency in the changes over time between the endpoints will also be assessed.

The ESSDAI, stimulated salivary flow, oral dryness numeric response scale and salivary gland B cell quantification change from baseline scores will be statistically analysed using a repeated measures MMRM analysis, comparing the belimumab/rituximab or the belimumab monotherapy arm with placebo at each time point. Similar analyses will also be conducted, if deemed appropriate, comparing each monotherapy arm with placebo. The baseline ESSDAI scores will be investigated as a potential co-variate in the model, if deemed appropriate.

In addition, based on the data that we observe in the study, probabilities of success will be determined. For example, what is the probability that we would observe a certain change in the ESSDAI score (i.e., comparator rate), based on the data that we have observed in the study.

Health Outcome Analyses

Pain, dryness, and fatigue will be assessed over time using the ESSPRI total score and subscale scores. In addition, the PROFAD-SSI-SF will assess fatigue, discomfort and Sicca symptoms. The patient and physician global assessments (PGA) will be performed to assess disease activity. At the end of the study, patients will participate in an exit interview where they will be asked to report on their experience with treatment during the clinical trial. Questions will be asked regarding treatment benefit, side effects, and study design (in terms of patient burden). The interview data will be qualitatively analysed and will serve to inform expected magnitude of treatment benefit, risk tolerance, and future study design considerations.

All health outcome measures will be listed, summarized and presented graphically over time where appropriate.

Pharmacokinetic Analyses

Serum belimumab and/or rituximab concentration data obtained from this study may also be used in a population PK analysis, which may also include data from other studies and may be reported separately.

Pharmacokinetics/Pharmacodynamic Analyses

Exploratory plots will be presented for belimumab and rituximab serum concentrations versus each of the key secondary endpoints (ESSDAI, stimulated salivary flow, oral dryness numeric response scale and salivary gland B cell quantification) and possibly for additional biomarkers at selected time points.

If deemed appropriate, further PK/PD modelling may be performed based on the results of the exploratory graphical analysis showing obvious relationships or trends between blood concentrations and the level of biomarkers in blood and also in the salivary gland biopsy. The choice of the structural pharmacokinetic/pharmacodynamic model will be dependent on the emerging data.

Example 2

This prophetic example relates to a proposed Phase 3, multi-center, 3-arm, randomized, double-blind, placebo-controlled, 104 week superiority study to evaluate the efficacy and safety of belimumab administered in combination with a single cycle of rituximab to adult subjects with SLE. There will be a primary 52 week double-blind treatment period followed by a 52 week treatment-free follow-up period.

Arms and Duration

In addition to receiving stable standard therapy at study entry, subjects will be randomized in a 1:1:1 ratio to one of the 3 arms. The 3 study arms are in Table 1.

TABLE 1

Study Dosing Scheme

| Treatment Arm | | Belimumab SC (via autoinjector) | Rituximab IV or Rituximab Placebo IV |
|---|---|---|---|
| A | Control | 200 mg/week for 52 weeks | RTX Placebo IV Week 4 and Week 6 |
| B | Combination | 200 mg/week for 52 weeks | RTX 1000 mg Week 4 and Week 6 |
| C | Reference | 200 mg/week for 104 weeks | NA |

Arm C (reference) is an open-label arm with belimumab subcutaneous (SC) injection 200 mg/week and standard therapy for 104 weeks. In this arm subjects who enter the study on immunosuppressants may continue these medications throughout the study. This arm will provide a qualitative reference to assess relative performance of arms A (control) and B (combination) vs. currently available standard SLE therapy.

At randomization, subjects will be stratified by their screening SLEDAI 2K score (≤9 vs. ≥10), by immunosuppressant use at screening (immunosuppressant use vs. no use) and by screening corticosteroid dose (prednisone equivalent ≤10 mg/day vs. >10 mg/day). Belimumab will be administered SC on Day 0 and then weekly (i.e., every 7 days±1 day) through week 51 for arms A and B, and through week 103 for arm C. SC injections will be administered at alternating injections sites between the left or right thighs and the abdomen. Rituximab or placebo will be administered by IV infusions at weeks 4 and 6 for arms A and B. The primary efficacy endpoint will be measured at week 52. In arms A and B a pre-medication regimen will be administered 30 minutes before each rituximab/rituximab placebo infusion on weeks 4 and 6, including: methylprednisolone 100 mg IV, an oral antihistamine and analgesic.

Belimumab SC 200 mg/week will be initiated in all 3 arms on day 0 of the study. Subjects in arms A and B who enter the study on immunosuppressant therapy will continue their stable regimen until week 4. At week 4, immunosuppressants will be discontinued, prior to the week 4 dose of the rituximab or rituximab-placebo study treatment. Continuing the stable immunosuppressant dose until week 4 allows subjects to receive 4 weeks of belimumab SC prior to discontinuing their immunosuppressants. Corticosteroids may be adjusted as necessary during this transition period. If subjects in arms A and B receive immunosuppressants after week 4 they will be deemed treatment failures. Subjects in arm C will continue their stable immunosuppressants throughout the study at the discretion of the investigator. If subjects in arm C require an increased dose of their stable immunosuppressant or addition of a new immunosuppressant they will be considered a treatment failure.

After the initial 12 weeks of the study, a protocol specified corticosteroid taper will be initiated and conducted under the direction of the investigator for subjects in all 3 arms. The taper will proceed with a target of reaching a prednisone equivalent dose of mg/day by week 26. If the investigator believes the subject would benefit from continued steroid taper and if tolerated, a prolonged corticosteroid taper should continue after week 26 with the goal of corticosteroid discontinuation. Subjects who are able to tolerate the final taper will be withdrawn from corticosteroids. If a subject is unable to tolerate the final stage of the corticosteroid taper, the investigator may reinitiate corticosteroids at a prednisone equivalent dose of up to and including 5 mg/day. If a prednisone equivalent dose of >5 mg/day is required at any time after week 26 the subject will be considered a treatment failure for the efficacy endpoints.

Anti-malarial therapies may be continued or dose adjusted during the study, and will be allowed within the definitions of the efficacy endpoints. However, by week 26, immunosuppressants and corticosteroids at prednisone equivalent dose of >5 mg/day will not be allowed.

During the 52 week double-blind portion of the study, subjects in arms A and B who cannot tolerate discontinuation of immunosuppressants or corticosteroid taper, or in the opinion of the investigator require added therapy, will be considered treatment failures for the efficacy endpoints. Blinding to the treatment assignments in arms A and B will be maintained. At the investigator's discretion, these subjects may continue treatment with belimumab, and/or be treated with additional therapies as necessary, including corticosteroids or immunosuppressants. Subjects in arm C who are unable to tolerate the corticosteroid taper, or who in the opinion of the investigator require increased doses of their baseline immunosuppressants or addition of a new immunosuppressant will be considered treatment failures for the efficacy endpoints.

Subjects from any arm who are deemed treatment failures at any time during the study will remain in the study and continue to have all efficacy and safety assessments.

Subjects in arms A and B who successfully complete the initial 52-week double-blind phase will enter into the 52-week treatment-free, follow-up phase of this study (weeks 53 through 104). "Treatment free" refers to no active treatment with study treatment (i.e., belimumab and/or rituximab). Subjects in arm C will continue to receive belimumab SC and their stable immunosuppressants during weeks 53 through 104. Treatment with anti-malarials, NSAIDs, and/or corticosteroids with a prednisone equivalent dose of mg/day will be allowed. Subjects participating in the follow-up phase will continue to be monitored for safety and efficacy.

In the follow-up phase of the study, additional treatment may be given if the investigator believes a subject would benefit because they have: a) responded to study treatment but did not meet the primary efficacy endpoint, or b) responded to study treatment but subsequently experienced increasing disease activity which requires additional therapy. Treatment may include open-label belimumab, corticosteroids, and/or immunosuppressants and will be administered at the discretion of the investigator. These subjects will be considered treatment failures for the week 104 efficacy analyses. Subjects who are deemed treatment failures will continue to be followed in the study and have all efficacy and safety assessments.

The invention claimed is:

1. A method of treatment of an autoimmune disorder comprising administering to a human in need thereof an effective amount of a CD20 binding antibody which is capable of depleting B cells, and a BLyS binding antibody which is capable of antagonizing BLyS, wherein:
   the BLyS binding antibody is administered to the human in need thereof for a period of at least 12 weeks;
   the CD20 binding antibody is administered to the human in need thereof at least once, and the CD20 binding antibody is not administered before the first dose of the BLyS binding antibody;
   the administration of the BLyS binding antibody continues for at least 4 weeks after the last dose of the CD20 binding antibody;
   wherein the autoimmune disorder is vasculitis;
   wherein the CD20 binding antibody is rituximab; and
   the BLyS binding antibody is belimumab.

2. The method according to claim 1, wherein the CD20 binding antibody is administered to the human in need thereof at least two weeks after the first dose of the BLyS binding antibody.

3. The method according to claim 1, wherein the CD20 binding antibody is administered to the human in need thereof at least twice between weeks 2 and 20 after the first dose of the BLyS binding antibody.

4. The method according to claim 1, wherein the BLyS binding antibody is administered to the human in need thereof once per week.

5. The method according to claim 1, wherein the BLyS binding antibody is administered to the human in need thereof for a period of 24 weeks.

6. The method according to claim 1, wherein the BLyS binding antibody is administered to the human in need thereof for a period of 52 weeks.

7. The method according to claim 1, wherein the belimumab is administered as a subcutaneous injection.

8. The method according to claim 7, wherein the belimumab is administered at a dosage of 200 mg.

9. The method according to claim 1, wherein the rituximab is administered as an intravenous infusion.

10. The method according to claim 9, wherein the rituximab is administered at a dosage of 1000 mg.

* * * * *

UNITED STATES PATENT AND TRADEMARK OFFICE
CERTIFICATE OF CORRECTION

PATENT NO. : 12,060,431 B2
APPLICATION NO. : 17/519063
DATED : August 13, 2024
INVENTOR(S) : Robert B. Henderson It is certified that error appears in the above-identified patent and that said Letters Patent is hereby corrected as shown below:

On the Title Page

In item:
(54) and in the Specification Column 1, Line 2 Please delete "ANTICD20" and insert in place thereof --ANTI-CD20--
(30) Please delete "Sep. 25, 2015" and insert in place thereof --Sep. 23, 2015--

Signed and Sealed this
Eighth Day of October, 2024

Katherine Kelly Vidal
*Director of the United States Patent and Trademark Office*